United States Patent [19]

Sadé et al.

[11] Patent Number: 5,163,957

[45] Date of Patent: Nov. 17, 1992

[54] OSSICULAR PROSTHESIS FOR MOUNTING MAGNET

[75] Inventors: Yacov Sadé, Ramat Hasharon, Israel; T. Manford McGee, Franklin, Mich.; Harlan J. Reitan, Collierville; Jorgen Heide, Memphis, both of Tenn.

[73] Assignee: Smith & Nephew Richards, Inc., Memphis, Tenn.

[21] Appl. No.: 757,246

[22] Filed: Sep. 10, 1991

[51] Int. Cl.5 ............................................. A61F 2/18
[52] U.S. Cl. .................................. 623/10; 128/420.6; 381/68.3
[58] Field of Search ............................ 623/10; 600/25; 128/419 R, 420.5, 420.6; 381/68.3, 151

[56] References Cited

U.S. PATENT DOCUMENTS 4,776,322 10/1988 Hough et al. ................... 128/420.6
4,840,178 6/1989 Heide et al. ........................ 381/68.3
4,936,305 6/1990 Ashtiani et al. ................... 128/420.6

Primary Examiner—Randy C. Shay
Attorney, Agent, or Firm—Pravel, Gambrell, Hewitt, Kimball & Krieger

[57] ABSTRACT

A prosthesis for use with an intact ossicular chain to allow a magnet to be coupled to the ossicular chain, the magnet being moved by an electromagnetic induction hearing aid. The prosthesis has a body having a first groove which cooperates with the manubrium and a second groove formed by an arm extending from the body and a hooked end, the second groove cooperating with the long process. A magnet is connected to a planar surface developed by the arm and the hooked end and is generally parallel to the tympanic membrane when installed. A conventional disk shaped magnet can be utilized inside a biocompatible housing.

16 Claims, 2 Drawing Sheets

OSSICULAR PROSTHESIS FOR MOUNTING MAGNET

BACKGROUND OF THE INVENTION

1. Field of the Invention

The present invention relates to a prothesis for use in the middle ear, and more particularly, to a prothesis for holding a magnet for use with an electromagnetic induction hearing aid.

2. Description of the Related Art

One common problem with in-the-ear acoustic hearing aids has been low fidelity. This low fidelity results from the very small size of the receiver or speaker, standing waves created in the ear canal and feedback because of the venting of the hearing aid. An alternative to resolve this problem has been the use of an electromagnetic induction hearing aid, wherein a magnet is coupled to the ossicles of the middle ear, the tympanic membrane or the cochlea and driven into motion by an electromagnetic field produced by an output coil in the hearing aid. This concept was first proposed by Rutschmann in an article entitled "Magnetic Audition—Auditory Stimulation by means of Alternating Magnetic Fields Acting on a Permanent Magnet Fixed to the Eardrum," IRE Transactions on Medical Electronics, Mar. 1959, pp. 22-23. Further work indicating promise was done by Richard L. Goode as indicated in his two articles "An Implantable Hearing Aid," Tr. Am. Acad. Ophthalmol & Otholaryngol, 74:128-139, Jan.-Feb. 1970 and "Audition via Electromagnetic Induction," Arch Otolarnygol, 98:23-26, Jul. 1973. Goode in most of his tests glued a magnet to the tympanic membrane which was then vibrated by either a coil located behind the ear or a special, externally driven coil inserted in the ear canal. In other tests Goode temporarily affixed the magnet to various locations in the middle ear and affixed the magnet to a Silverstein malleus clip. Goode indicated the feasibility and desire to develop such as system. A similar system was shown in Belgium U.S. Pat. No. 833,809, which was published on Mar. 25, 1976.

The field lay basically dormant for a number of years until work was commenced by Drs. Jack Hough, Jack Vernon and Kenneth Dormer and Messrs. Jorgen Heide, Anthony Prescott and Timothy Gooch. The work of these two groups resulted in a series of U.S. Pat. Nos., 4,606,329, 4,776,322 and 4,800,884. These patents show various behind the ear and in the ear versions of hearing aids which have coils which develop magnetic fields which are coupled to magnets located in the middle ear or coupled to the ossicles.

One problem with electromagnetic induction has been that magnet materials are basically not bio-compatible, especially the magnet materials having sufficient energy densities so that higher efficiency and therefore longer battery life can be obtained. To this end some method or means of bio-compatibility has been required. Hough, et al. indicated in the various patents that the magnet material could be impregnated into a bio-compatible material and formed into a prosthesis having various shapes as shown in the patents. Other alternatives for magnet placement were shown in Heide Pat. No. 4,800,884. One embodiment was the use of a magnet located at the end of a Silverstein malleus clip, with the clip passing through the tympanic membrane and being coupled to the malleus. In a second embodiment a biocompatibly coated magnet was located between the tympanic membrane and the malleus. Various other designs have been developed to couple the magnet to the ossicles. For example, in U.S. Pat. No. 4,817,607 to Tatge, the magnet is located in the head of a partial or total ossicular replacement prosthesis. Alternatively, in U.S. Pat. No. 4,840,178 to Heide et al. the magnet is formed in two pieces which are hinged together and clasp around the long process of the incus. Yet another variation is shown in U.S. Pat. application Ser. No. 702,396 to Heide et al., where the magnet is removably attached to a transtympanic rod which passes through the tympanic membrane and is affixed to the malleus either by means of a snug fit into a hole drilled in the malleus or a clamp around the malleus.

While there are thus numerous variations shown for coupling the magnet to the ossicles, there are disadvantages in several cases and other cases which are not adequately covered by the known protheses. For example, in many cases the patient has a fully functional ossicular chain and therefore the use of a replacement prothesis as shown Tatge or Hough is not desirable. Further, the magnets and prothesis as shown in Heide '178 and Hough are quite difficult to construct because of the unusual shapes of the magnetic materials. Other variations pass through the tympanic membrane, which while reducing biocompatibility concerns, does have the problem that the tympanic membrane has been traversed and this may be undesirable for a long term installation in some cases.

Therefore it is desirable to have a prosthesis which allows operation of a fully intact ossicular chain, does not require convoluted and complicated magnet shapes and is wholly contained in the middle ear cavity.

SUMMARY OF THE INVENTION

A prosthesis according to the present invention is designed to be totally self contained in the middle ear cavity and is connected to the manubrium and long process of the incus and includes a means for locating and retaining a conventionally shaped magnet. The prosthesis contains two channels or grooves, one for contacting the manubrium of the malleus and the other for hooking around the long process of the incus. A generally planar shelf area is provided approximately near the long process of the incus and generally parallel to the tympanic membrane for receiving the magnet. Preferably the magnet is contained in a titanium canister for biocompatibility reasons. The prosthesis is preferably formed of hydroxyapatite, polytetraflouroethylene or other materials which are stable and biocompatible. The prosthesis has various radius curves and appropriate spacing so that it can be utilized in a variety of middle ear cavities with only a few variations in the actual design and sizing. Further, the prosthesis is designed not to interfere with actual movement of the ossicular chain, so that conventional acoustic transmission is still developed in a middle ear containing the prosthesis.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENT

Figure 1:
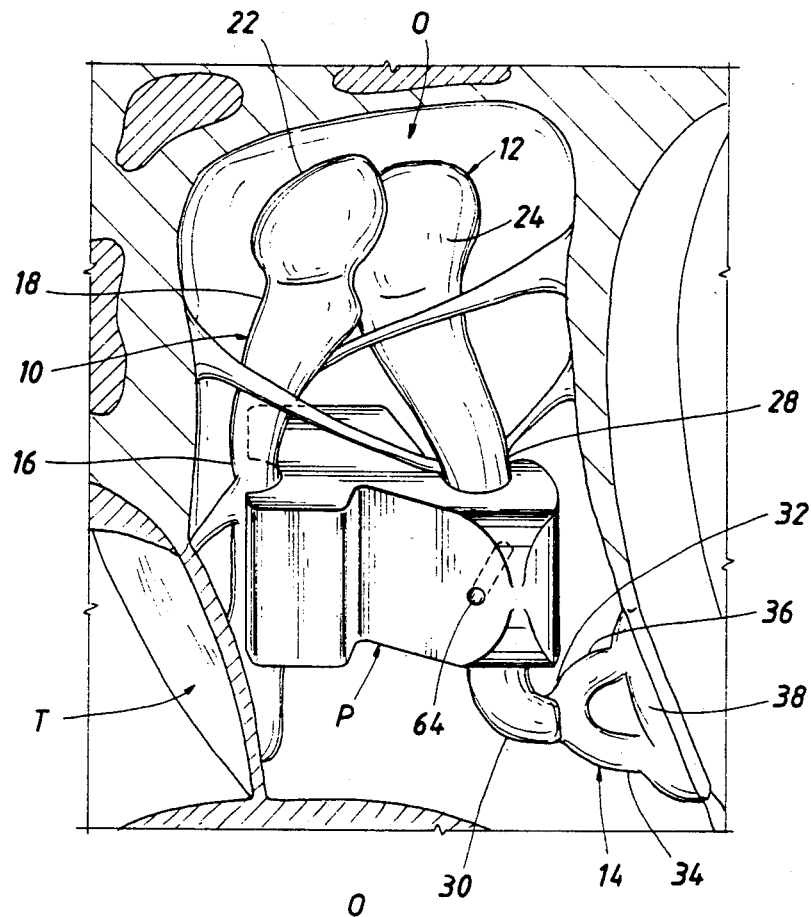
FIG. 1 is a perspective view of a middle ear cavity including the ossicular chain and a prosthesis according to the present invention.

Referring now to FIG. 1, the ossicular chain, generally referred to by the letter O, is shown in conjunction with a prosthesis P according to the present invention. The ossicular chain includes the malleus 10, the incus 12 and the stapes 14. The malleus 10 comprises several portions, including the manubrium 16, the neck 18 and the head 22. The incus 12 has a body 24 connected to the head 22 of the malleus 10. The incus 12 further includes a long process 28 and a lenticular process 30. The long process 28 is generally parallel with the manubrium 16. The lenticular process 30 is connected to the head 32 of the stapes 14. The head 32 is also connected to the anterior and posterior crus 34 and 36, which in turn are connected to the footplate 38. The footplate 38 rests on the oval window, which is the boundary and separating membrane between the middle ear and the cochlea. The prosthesis P as shown, contacts the manubrium 16 and the long process 28.

Figure 2:
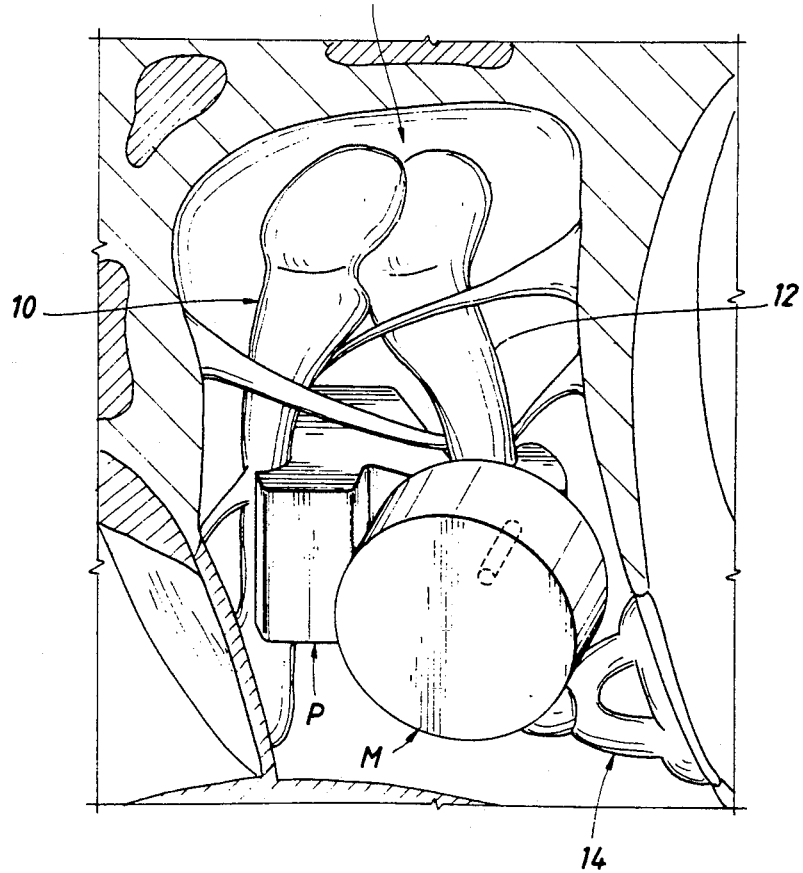
FIG. 2 is the view of FIG. 1 with a magnet installed on the prosthesis.

Referring now to FIG. 2, a magnet assembly M is shown attached to the prosthesis P to allow visualization of the orientation with respect to the ossicular chain 0.

Figure 3:
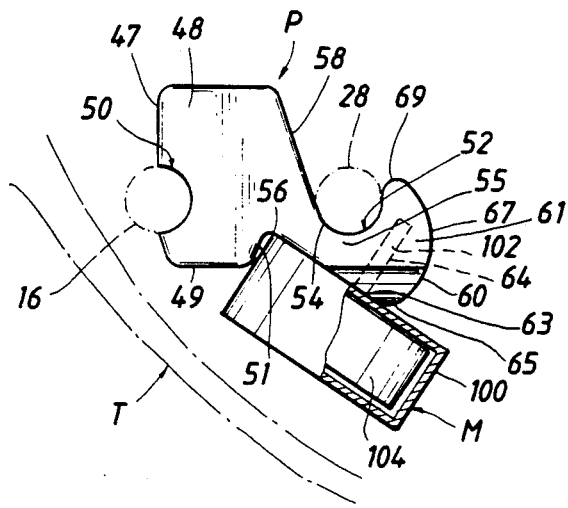
FIG. 3 is a top view in partial cross-section of the prosthesis and magnet of FIG. 2.

Referring to FIG. 3, a top view of the various elements is shown. As can be seen, the manubrium 16 is connected to the tympanic membrane T. Further, it can be seen that the manubrium 16 and the long process 28 of the incus 12 are not perpendicular to the tympanic membrane T but are slightly displaced. The prosthesis P has a body 48 which includes a first groove 50, which mates with the manubrium 16. The body 48 is a generally rectangular parallelepiped. The front portion 49 of the body 48 is generally angled inwardly, preferably at an angle of approximately 21° on the manubrium side face 47 and approximately 20° on the long process side face 51. Preferably the body 48 is approximately 0.094 inches from front to rear and approximately 0.060 inches wide at the rear.

Projecting from the rear of the body 48 towards the long process 28 is an arm 54. The arm 54 has a generally planar front surface 56 and a generally planar rear surface 58, with the front and rear surfaces 56 and 58 generally converging to form a neck 55. The front surface 56 is substantially parallel to the tympanic membrane T when the prosthesis P is installed and is preferably approximately 57° from the side face 47 of the body 48. A protruding hook 60 is connected to the neck 55 of the arm 54. A combination of the rear surface 58 and the inner surface 62 of the hook 60 form a second groove 52 which cooperates with the long process 28. The second groove 52 has an inner radius appropriate to cooperate with the long process 28, preferably an inner radius of approximately 0.018 inches. The hook 60 includes an enlarged head 61 including a portion 63 of the front surface 56 and containing a hole 64 in the front surface portion 63. The hook 60 is generally curved in three dimensions to allow it to clear the various portions of the surface which defines the middle ear cavity. The hook 60 has a transitional portion 65 between the front surface portion 63 and the outer curved portion 67. Preferably the radius of the transitional portion 65 is approximately 0.012 inches, of the outer curved portion 67 is approximately 0.039 inches and of the tip portion 69 is approximately 0.08 inches. The prosthesis P is preferably formed of biocompatible materials such as hydroxyapatite, polytetraflouroethylene, ultra high molecular weight polyethylene and similar materials.

The magnet assembly M includes a housing 100, preferably formed of titanium or other biocompatible, non-magnetic material. Preferably the housing 100 is cylindrical. Protruding from the housing 100 is a rod 102 which mates with the hole 64 in the hook 60. Contained within the housing 100 is magnet material 104. Preferably the magnet material 104 is a high energy material such as samarium cobalt or neodymium boron iron, so that the efficiency of the hearing aid is increased. Other high energy magnetic materials may be used. Preferably the magnet material 104 is formed in a disk so that conventional magnet construction techniques can be utilized. The magnet assembly M is preferably installed on the prosthesis P by locating a small drop of silicone or other biocompatible adhesive on the front surface 56 and inserting the rod 102 into the hole 64 until the magnet assembly M contacts the prothesis P.

Figure 6:
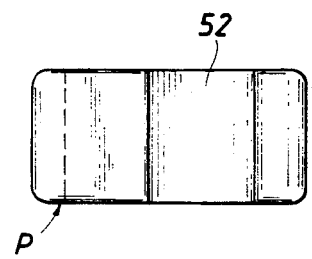
FIGS. 4, 5 and 6 are top, side and rear views of the prosthesis of FIG. 1.
Figure 5:
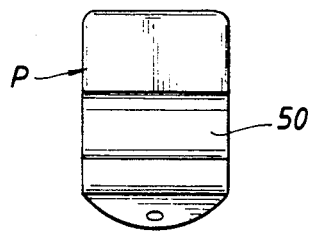
Figure 4:
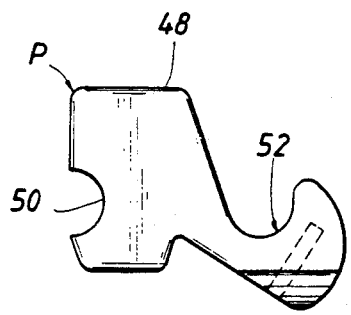

Side and rear projections of the prosthesis P can be seen in FIGS. 5 and 6, respectively. The prosthesis P is preferably approximately 0.075 inches thick, thus accommodating the majority of ossicles without interfering with ossicle movement and yet providing sufficient surface area for a positive fit with the manubrium 16 and the long process 28. While the body 48 is generally planar in the vertical direction, the hook 60 is curved, preferably at a radius of approximately 0.048 inches, measured from the center line of the groove 50. This curve allows further clearance when installed in the middle ear.

Figure 7:
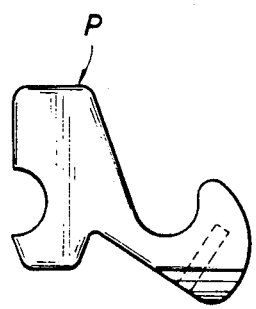
FIGS. 7 and 8 are top views of alternate embodiments of a prosthesis according to the present invention.
Figure 8:
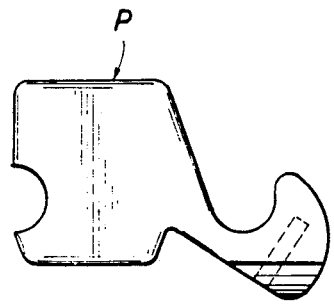

FIGS. 7 and 8 show top views of alternative embodiments the prosthesis P wherein the body 48 has different widths. The body width is varied to account for individual differences in the spacing between the manubrium 16 and the long process 28. For example, in the prosthesis P of FIG. 7, the rear face is approximately 0.040 inches wide, while on the prosthesis P of FIG. 8 the rear face is approximately 0.080 inches wide. At this time is contemplated that only three particular sizes are necessary to handle the majority of ossicular chains, but other sizes can be developed if necessary.

Installation of the prosthesis P is readily accomplished. The side face 47 of the body 48 and the rear surface 58 of the arm 54 form a wedge so that the prosthesis P can be placed between the manubrium 16 and long process 28. Force is then applied until the grooves 50 and 52 are properly located. The prosthesis P is then retained in the ossicular chain 0 without need of adhesive materials. This allows the ossicular chain O to freely vibrate due to acoustic transfer through the tympanic membrane T. The magnet assembly M can be installed in the prosthesis P before or after installation of the prosthesis P in the middle ear. The location of the prosthesis P between the manubrium 16 and the long process 28 allows the magnet assembly M to vibrate in response to the electromagnetic field produced by the hearing aid and cause the long process 28 to vibrate so that the stapes 14 is moved, which in turn causes perception of sound in the patient via the cochlea.

Having described the invention above, various modifications of the techniques, procedures, material and equipment will be apparent to those in the art. It is intended that all such variations within the scope and spirit of the appended claims be embraced thereby.

What is claimed is:

1. A middle ear prosthesis for contacting the ossicular chain for mounting a magnet used with an electromagnetic induction hearing aid to allow the ossicular chain in the middle ear cavity to remain intact and yet be moved by the magnet, the prosthesis comprising:

a body portion which is generally a rectangular parallelepiped and including a groove in one face, said groove shaped to cooperate with the manubrium;

an arm portion connected to said body portion and extending from the face opposite said manubrium groove; and a hook portion connected to said arm portion and generally having an inner arc and an outer arc, said inner arc cooperating with said arm portion to form a groove, said groove shaped to cooperate with the long process, said arm portion and said hook portion further cooperating to provide a generally planar surface for receiving the magnet.

2. The prosthesis of claim 1, wherein said hook portion includes a hole developed in said surface for receiving the magnet.

3. The prosthesis of claim 1, wherein said arm portion tapers from the connection point to said body portion to the connection point to said hook portion.

4. The prosthesis of claim 3, wherein said arm portion is broader at the body portion connection and narrower at the hook portion connection.

5. The prosthesis of claim 1, wherein said body portion has a width sized such that said manubrium groove and said long process groove are spaced to approximately match the spacing between the manubrium and the long process.

6. The prosthesis of claim 1, wherein said hook portion is approximately curved to provide clearance between said hook portion and the surface defining the middle ear cavity when the prosthesis is installed.

7. A middle ear prosthesis for contacting the ossicular chain for use with an electromagnetic induction hearing aid to allow the ossicular chain to remain intact, the prosthesis comprising:

a magnet;

a body portion which is generally a rectangular parallelepiped and including a groove in one face, said groove shaped to cooperate with the manubrium;

an arm portion connected to said body portion and extending from the face opposite said manubrium groove; and a hook portion connected to said arm portion and generally having an inner arc and an outer arc, said inner arc cooperating with said arm portion to form a groove, said groove shaped to cooperate with the long process, said arm portion and said hook portion further cooperating to provide a generally planar surface receiving said magnet.

8. The prosthesis of claim 7, wherein said hook portion includes a hole developed in said magnet receiving surface and said magnet includes a projection inserted in said hole.

9. The prosthesis of claim 7, wherein said arm portion tapers from the connection point to said body portion to the connection point to said hook portion.

10. The prosthesis of claim 9, wherein said arm portion is broader at the body portion connection and narrower at the hook portion connection.

11. The prosthesis of claim 7, wherein said body portion has a width sized such that said manubrium groove and said long process groove are spaced to approximately match the spacing between the manubrium and the long process.

12. The prosthesis of claim 7, wherein said hook portion is approximately curved to provide clearance between said hook portion and the surface defining the middle ear cavity when the prosthesis is installed.

13. The prosthesis of claim 7, wherein said magnet includes magnetic material and a biocompatible housing surrounding said magnetic material.

14. The prosthesis of claim 13, wherein said magnetic material is generally disk shaped.

15. The prosthesis of claim 13, wherein said magnetic material is generally comprised of samarium cobalt.

16. The prosthesis of claim 13, wherein said housing is comprised of titanium.

* * * * *